US012573218B2

(12) United States Patent
Aghdam et al.

(10) Patent No.: US 12,573,218 B2
(45) Date of Patent: Mar. 10, 2026

(54) SYSTEMS AND METHODS FOR PROCESSING ELECTRONIC IMAGES FOR RANKING LOSS AND GRADING

(71) Applicant: PAIGE.AI, INC., New York, NY (US)

(72) Inventors: Hamed Aghdam, New York, NY (US); Christopher Kanan, Pittsford, NY (US)

(73) Assignee: Paige.AI, Inc., New York, NY (US)

( * ) Notice: Subject to any disclaimer, the term of this patent is extended or adjusted under 35 U.S.C. 154(b) by 450 days.

(21) Appl. No.: 18/161,688

(22) Filed: Jan. 30, 2023

(65) Prior Publication Data

US 2023/0245480 A1 Aug. 3, 2023

Related U.S. Application Data

(60) Provisional application No. 63/305,150, filed on Jan. 31, 2022.

(51) Int. Cl.
| | |
|---|---|
| *G06V 20/69* | (2022.01) |
| *G06T 7/00* | (2017.01) |
| *G06T 7/11* | (2017.01) |
| *G16H 50/30* | (2018.01) |

(52) U.S. Cl.
CPC .......... *G06V 20/698* (2022.01); *G06T 7/0012* (2013.01); *G06T 7/11* (2017.01); *G16H 50/30* (2018.01); *G06T 2207/20021* (2013.01); *G06T 2207/20081* (2013.01); *G06T 2207/30024* (2013.01)

(58) Field of Classification Search
CPC .............................. G06T 20/698; G16H 50/30
See application file for complete search history.

(56) References Cited

U.S. PATENT DOCUMENTS

2021/0209753 A1* 7/2021 Dogdas ................ G06V 20/698
2022/0005201 A1 1/2022 Rothrock et al.

FOREIGN PATENT DOCUMENTS

WO 2020243090 A1 12/2020

OTHER PUBLICATIONS

Li et al., "An attention-based multi-resolution model for prostate whole slide image classification and localization", CVPR, 2019, pp. 1-8 (Year: 2019).*
Kalapahar, et al., "Gleason Grading of Histology Prostate Images Through Semantic Segmentation Via Residual U-Net", IEEE, 2020, pp. 2501-2505 (Year: 2020).*

(Continued)

*Primary Examiner* — Edward Park
(74) *Attorney, Agent, or Firm* — Bookoff McAndrews, PLLC

(57) ABSTRACT

A computer-implemented method for processing medical images, the method comprising receiving a plurality of medical images of at least one pathology specimen, the pathology specimen being associated with a patient. The method may further comprise dividing the one or more medical images into a plurality of tiles and predicting, using a machine learning system, proportions of each type of cancer sub-category for the plurality of tiles, the machine learning system having been trained by ranking loss. The method may further include determining an overall grade of cancer for the one or more medical images.

20 Claims, 10 Drawing Sheets

(56)             References Cited

OTHER PUBLICATIONS

Le Vuong, T.T., Kim, K., Song, B., Kwak, J.T. (2021). "Ranking Loss: A Ranking-Based Deep Neural Network for Colorectal Cancer Grading in Pathology Images," Medical Image Computing and Computer Assisted Intervention—MICCAI 2021. Lecture Notes in Computer Science, vol. 12908. Springer, Cham. https://doi.org/10.1007/978-3-030-87237-3_52.

* cited by examiner

300

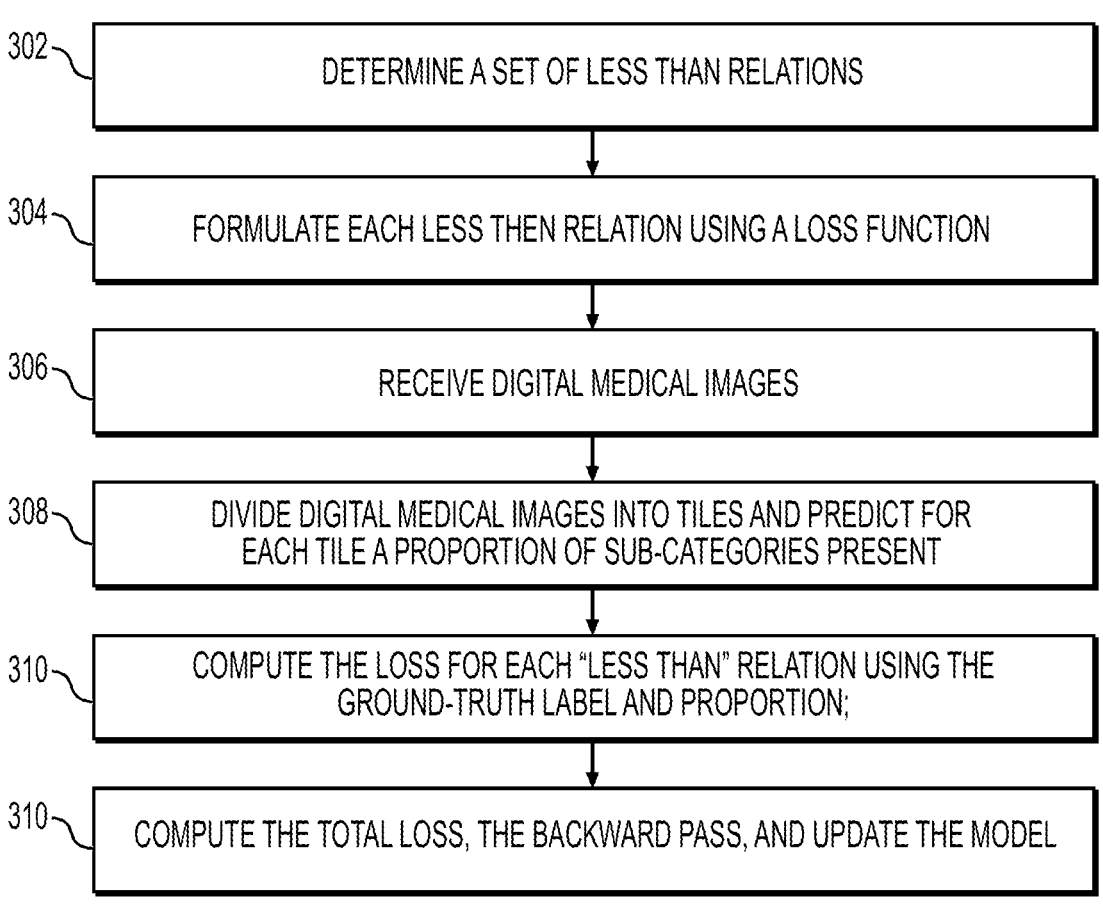

302 — DETERMINE A SET OF LESS THAN RELATIONS

304 — FORMULATE EACH LESS THEN RELATION USING A LOSS FUNCTION

306 — RECEIVE DIGITAL MEDICAL IMAGES

308 — DIVIDE DIGITAL MEDICAL IMAGES INTO TILES AND PREDICT FOR EACH TILE A PROPORTION OF SUB-CATEGORIES PRESENT

310 — COMPUTE THE LOSS FOR EACH "LESS THAN" RELATION USING THE GROUND-TRUTH LABEL AND PROPORTION;

310 — COMPUTE THE TOTAL LOSS, THE BACKWARD PASS, AND UPDATE THE MODEL

352 — RECEIVE DIGITAL MEDICAL IMAGES

354 — DIVIDE THE DIGITAL MEDICAL IMAGES INTO TILES

356 — PREDICT PROPORTIONS OF EACH SUB-CATEGORY

358 — DETERMINE A SCORE USING THE SET OF RULES AND PROPORTIONS OF EACH SUB-CATEGORY

400

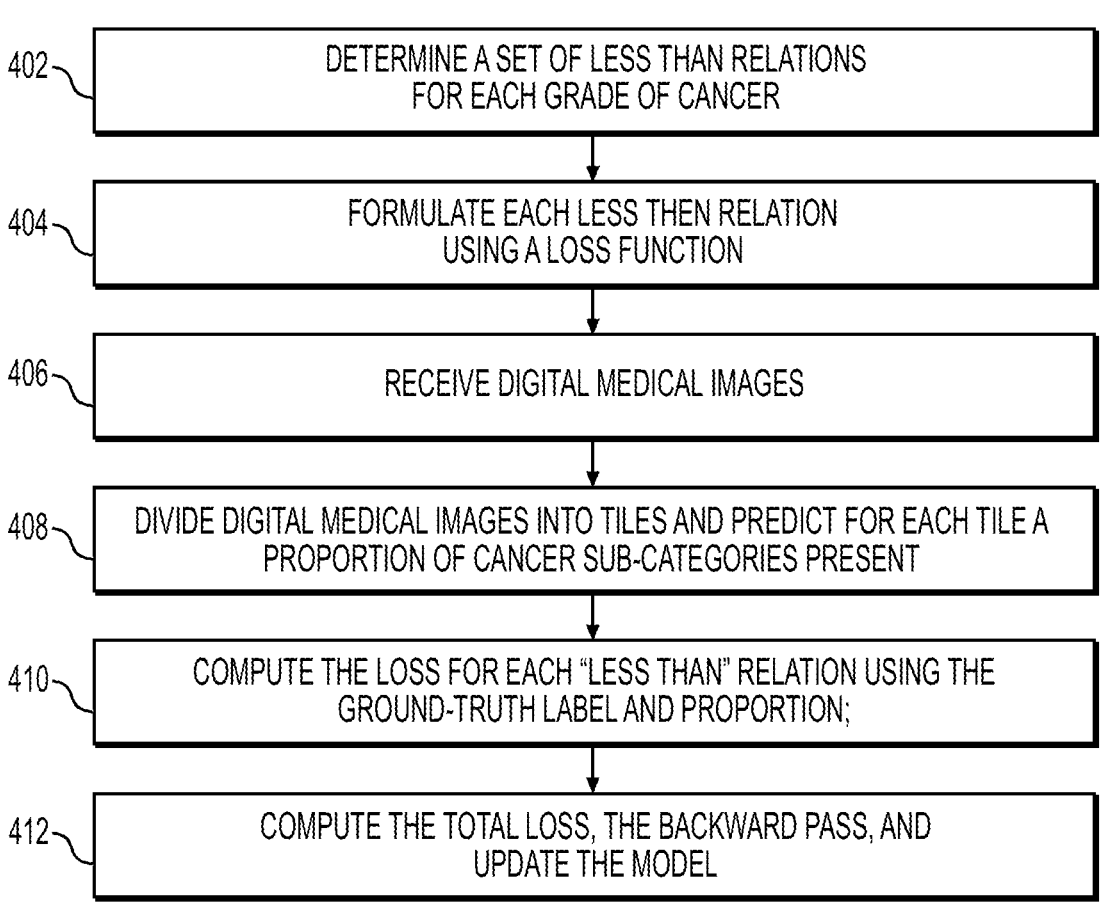

402 — DETERMINE A SET OF LESS THAN RELATIONS FOR EACH GRADE OF CANCER

404 — FORMULATE EACH LESS THEN RELATION USING A LOSS FUNCTION

406 — RECEIVE DIGITAL MEDICAL IMAGES

408 — DIVIDE DIGITAL MEDICAL IMAGES INTO TILES AND PREDICT FOR EACH TILE A PROPORTION OF CANCER SUB-CATEGORIES PRESENT

410 — COMPUTE THE LOSS FOR EACH "LESS THAN" RELATION USING THE GROUND-TRUTH LABEL AND PROPORTION;

412 — COMPUTE THE TOTAL LOSS, THE BACKWARD PASS, AND UPDATE THE MODEL

452 — RECEIVE DIGITAL MEDICAL IMAGE

454 — DIVIDE THE DIGITAL MEDICAL IMAGES INTO TILES

456 — PREDICT PROPORTIONS OF EACH CANCER SUB-CATEGORY

458 — DETERMINE A CANCER SCORE USING THE SET OF RULES AND PROPORTIONS OF EACH SUB-CATEGORY

500

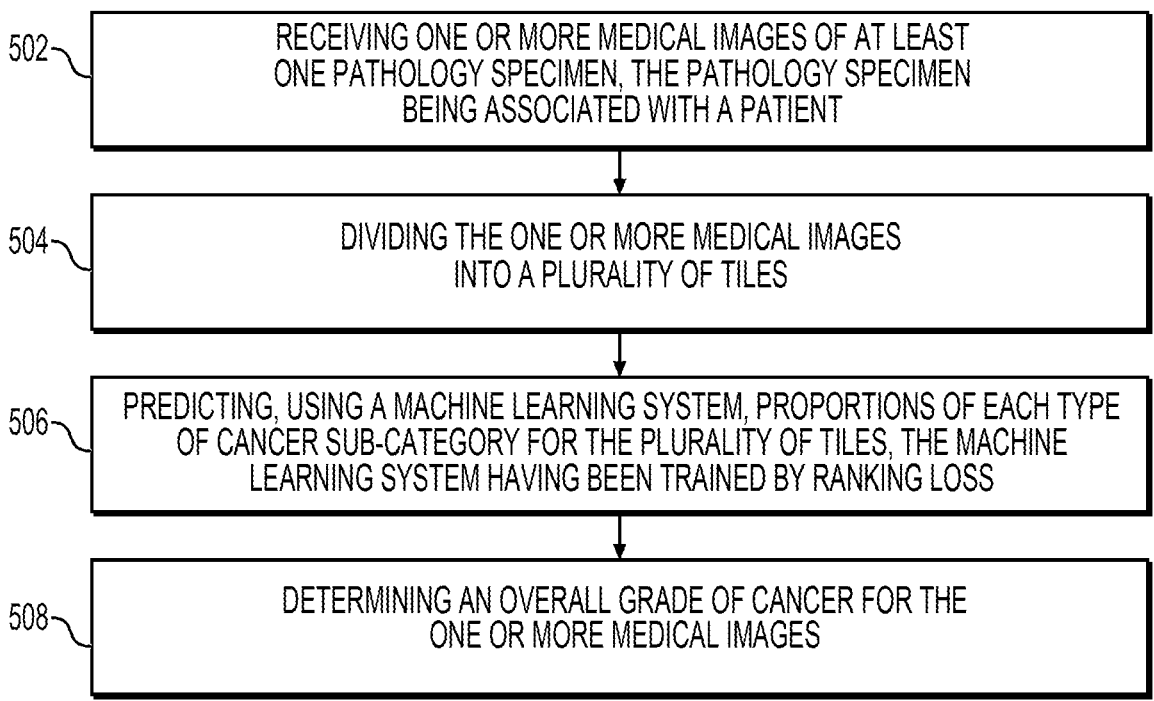

502 — RECEIVING ONE OR MORE MEDICAL IMAGES OF AT LEAST ONE PATHOLOGY SPECIMEN, THE PATHOLOGY SPECIMEN BEING ASSOCIATED WITH A PATIENT

504 — DIVIDING THE ONE OR MORE MEDICAL IMAGES INTO A PLURALITY OF TILES

506 — PREDICTING, USING A MACHINE LEARNING SYSTEM, PROPORTIONS OF EACH TYPE OF CANCER SUB-CATEGORY FOR THE PLURALITY OF TILES, THE MACHINE LEARNING SYSTEM HAVING BEEN TRAINED BY RANKING LOSS

508 — DETERMINING AN OVERALL GRADE OF CANCER FOR THE ONE OR MORE MEDICAL IMAGES

*FIG. 5*

SYSTEMS AND METHODS FOR PROCESSING ELECTRONIC IMAGES FOR RANKING LOSS AND GRADING

RELATED APPLICATION(S)

This application claims priority to U.S. Provisional Application No. 63/305,150 filed Jan. 31, 2022, the entire disclosure of which is hereby incorporated herein by reference in its entirety.

FIELD OF THE DISCLOSURE

Various embodiments of the present disclosure pertain generally to systems and methods for image processing. More specifically, particular embodiments of the present disclosure relate to systems and methods for processing electronic images for ranking loss and grading.

BACKGROUND

Many problems in machine learning relate to either classification or regression; however, these methods/algorithms might not capture relative severity relationships. Relative severity relationships are critical for many tasks in the field of medicine. For example, cancer grading represents the relative severity of the cancer diagnosis in terms of the predicted outcome for a patient. A patent's cancer grading may therefore have treatment implications. An example of cancer grading is a "Gleason pattern." Human experts compute proportions of "Gleason pattern" in prostate histopathology slides to grade the prostate cancer into a Gleason score category. Gleason scores provide information about proportions of Gleason patterns. For example, the 4+5 Gleason score means the dominant Gleason pattern is 4, Gleason pattern 5 corresponds to the highest pattern that exists in the tissue, and Gleason pattern 3 may or may not be present in the slide (the score provides no information as to the presence of Gleason pattern 3). Additionally, if Gleason pattern 3 is present, its proportion is less than Gleason pattern 4 but its proportion may or may not be less than Gleason pattern 5. Gleason score provides information on more than one Gleason pattern and the Gleason score encodes valuable information about the condition and severity of prostate cancer.

The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

According to certain aspects of the present disclosure, systems and methods are disclosed for processing electronic medical images, comprising: receiving one or more medical images of at least one pathology specimen, the pathology specimen being associated with a patient; dividing the one or more medical images into a plurality of tiles; predicting, using a machine learning system, proportions of each type of cancer sub-category for the plurality of tiles, the machine learning system having been trained by ranking loss; and determining an overall grade of cancer for the one or more medical images A system for processing electronic medical images, the system including: at least one memory storing instructions; and at least one processor configured to execute the instructions to perform operations comprising: receiving one or more medical images of at least one pathology specimen, the pathology specimen being associated with a patient; dividing the one or more medical images into a plurality of tiles; predicting, using a machine learning system, proportions of each type of cancer sub-category for the plurality of tiles, the machine learning system having been trained by ranking loss; and determining an overall grade of cancer for the one or more medical images.

A non-transitory computer-readable medium storing instructions that, when executed by a processor, perform operations processing electronic medical images, the operations comprising: receiving one or more medical images of at least one pathology specimen, the pathology specimen being associated with a patient; dividing the one or more medical images into a plurality of tiles; predicting, using a machine learning system, proportions of each type of cancer sub-category for the plurality of tiles, the machine learning system having been trained by ranking loss; and determining an overall grade of cancer for the one or more medical images.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 3A is a flowchart illustrating an example method for training an algorithm that uses a loss function to train a grading model, according to techniques presented herein.

FIG. 4A is a flowchart illustrating an example method for training an algorithm that uses a loss function to train a grading model based on various sub-classes of cancer, according to techniques presented herein.

FIG. 5 is a flowchart illustrating an example method for determining cancer subclasses using a machine learning system trained by ranking loss, according to techniques presented herein.

DESCRIPTION OF THE EMBODIMENTS

Figure 1A:
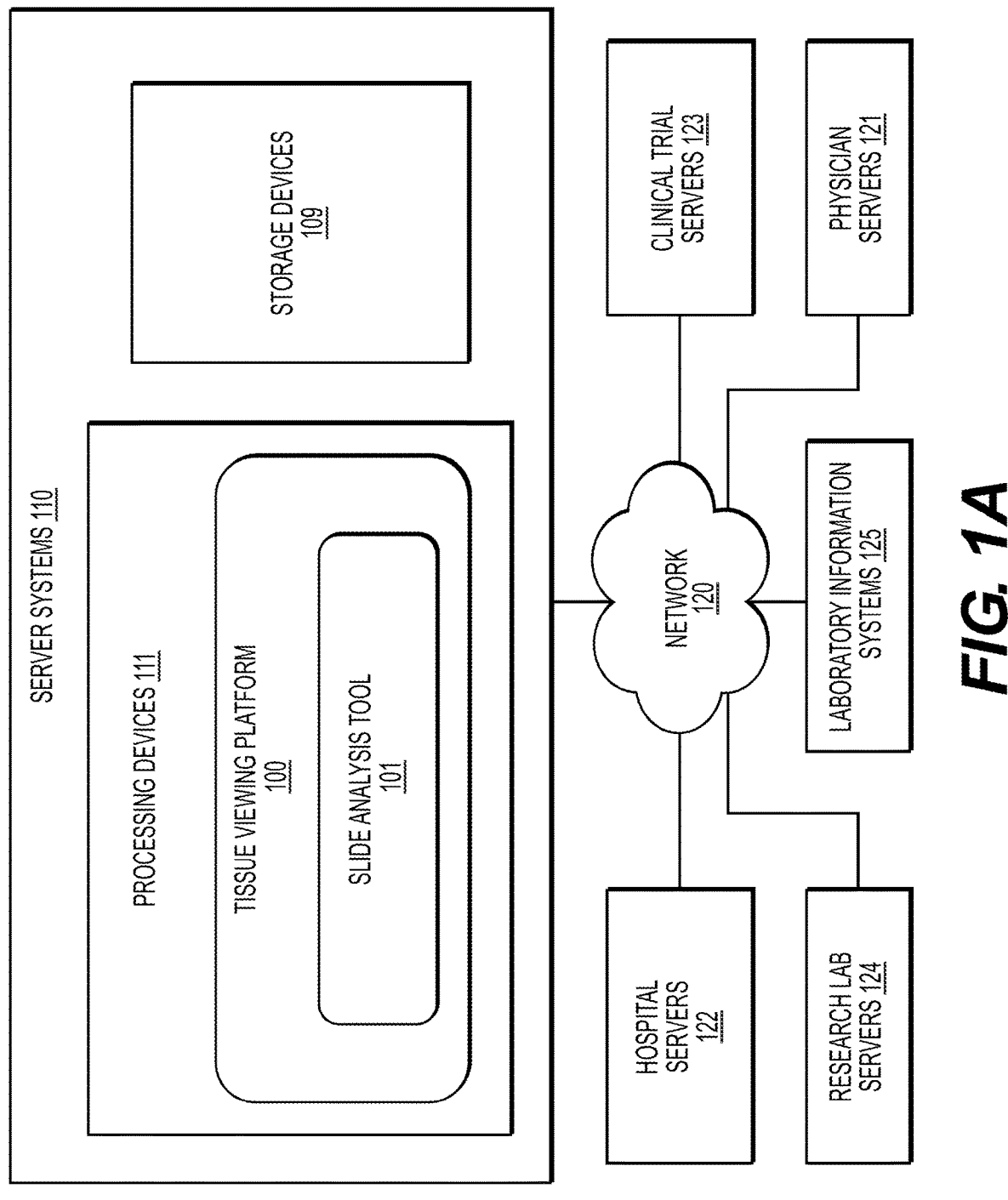
FIG. 1A illustrates an exemplary block diagram of a system and network for processing images, for example image matching, according to techniques presented herein.

Reference will now be made in detail to the exemplary embodiments of the present disclosure, examples of which are illustrated in the accompanying drawings. Wherever possible, the same reference numbers will be used through-out the drawings to refer to the same or like parts.

The systems, devices, and methods disclosed herein are described in detail by way of examples and with reference to the figures. The examples discussed herein are examples only and are provided to assist in the explanation of the apparatuses, devices, systems, and methods described herein. None of the features or components shown in the drawings or discussed below should be taken as mandatory for any specific implementation of any of these devices, systems, or methods unless specifically designated as man-datory.

Also, for any methods described, regardless of whether the method is described in conjunction with a flow diagram, it should be understood that unless otherwise specified or required by context, any explicit or implicit ordering of steps performed in the execution of a method does not imply that those steps must be performed in the order presented but instead may be performed in a different order or in parallel.

As used herein, the term "exemplary" is used in the sense of "example," rather than "ideal." Moreover, the terms "a" and "an" herein do not denote a limitation of quantity, but rather denote the presence of one or more of the referenced items.

As used herein, a "machine learning model" generally encompasses instructions, data, and/or a model configured to receive input, and apply one or more of a weight, bias, classification, or analysis on the input to generate an output. The output may include, for example, a classification of the input, an analysis based on the input, a design, process, prediction, or recommendation associated with the input, or any other suitable type of output. A machine learning model is generally trained using training data, e.g., experiential data and/or samples of input data, which are fed into the model in order to establish, tune, or modify one or more aspects of the model, e.g., the weights, biases, criteria for forming classifications or clusters, or the like. Deep learning techniques may also be employed. Aspects of a machine learning model may operate on an input linearly, in parallel, via a network (e.g., a neural network), or via any suitable configuration.

The execution of the machine learning model may include deployment of one or more machine learning techniques, such as linear regression, logistical regression, random for-est, gradient boosted machine (GBM), deep learning, and/or a deep neural network. Supervised and/or unsupervised training may be employed. For example, supervised learning may include providing training data and labels correspond-ing to the training data, e.g., as ground truth. Unsupervised approaches may include clustering, classification or the like. K-means clustering or K-Nearest Neighbors may also be used, which may be supervised or unsupervised. Combina-tions of K-Nearest Neighbors and an unsupervised cluster technique may also be used. Any suitable type of training may be used, e.g., stochastic, gradient boosted, random seeded, recursive, epoch, or batch-based, etc.

Annotating segmentation masks in whole slides images ("WSIs") manually may be a time-consuming process that requires human experts with deep domain knowledge. Drawing segmentation masks may become more challeng-ing when WSIs have multiple classes of cancer present (e.g., different cancer grades). The system described herein may solve this problem by training the system directly from diagnosis; however, rather to amplify the signal the system incorporates ranking information that accounts for the rela-tive severity of the diagnosis as reported by a pathologist or based on outcome.

Rather than formulating grading as a classification or ordinal regression problem, the system described herein translates the governing rules of grading into mathematical "greater than" and "less than" relations and innovates a new loss function to train the grading model based on proportions of various sub-classes of cancer in the slide. The "greater than" and "less than" relations may define the less severe morphology (e.g., the less than) versus more severe mor-phology (e.g., the greater than). For example, a morphologi-cal pattern that indicates a low-grade cancer would be "less than" a morphological pattern that indicates high-grade cancer.

As described in greater detail below, the system described herein may be capable of determining portions of Gleason pattern using the Gleason score of a slide and a machine learning system such as a convolutional neural network ("CNN") embedding extracted using a grading model, such as a prostate grading model. Further, the system may include utilizing pairwise ranking loss functions for each Gleason score. The machine learning system may minimize the loss functions described herein during training.

FIG. 1A illustrates a block diagram of a system and network for processing images to produce a low blur image, using machine learning, according to an exemplary embodi-ment of the present disclosure.

Specifically, FIG. 1A illustrates an electronic network 120 that may be connected to servers at hospitals, laboratories, and/or doctors' offices, etc. For example, physician servers 121, hospital servers 122, clinical trial servers 123, research lab servers 124, and/or laboratory information systems 125, etc., may each be connected to an electronic network 120, such as the Internet, through one or more computers, servers, and/or handheld mobile devices. According to an exemplary embodiment of the present disclosure, the electronic net-work 120 may also be connected to server systems 110, which may include processing devices that are configured to implement a tissue viewing platform 100, which includes a slide analysis tool 101 for determining specimen property or image property information pertaining to digital pathology image(s), and using machine learning to grade tissues of a specimen, according to an exemplary embodiment of the present disclosure.

The physician servers 121, hospital servers 122, clinical trial servers 123, research lab servers 124, and/or laboratory information systems 125 may create or otherwise obtain images of one or more patients' cytology specimen(s), histopathology specimen(s), slide(s) of the cytology speci-men(s), digitized images of the slide(s) of the histopathology specimen(s), or any combination thereof. The physician servers 121, hospital servers 122, clinical trial servers 123, research lab servers 124, and/or laboratory information systems 125 may also obtain any combination of patient-specific information, such as age, medical history, cancer treatment history, family history, past biopsy or cytology information, etc. The physician servers 121, hospital servers 122, clinical trial servers 123, research lab servers 124, and/or laboratory information systems 125 may transmit digitized slide images and/or patient-specific information to server systems 110 over the electronic network 120. Server systems 110 may include one or more storage devices 109 for storing images and data received from at least one of the physician servers 121, hospital servers 122, clinical trial servers 123, research lab servers 124, and/or laboratory information systems 125. Server systems 110 may also include processing devices for processing images and data stored in the one or more storage devices 109. Server systems 110 may further include one or more machine learning tool(s) or capabilities. For example, the processing devices may include a machine learning tool for a tissue viewing platform 100, according to one embodiment. Alternatively or in addition, the present disclosure (or portions of the system and methods of the present disclosure) may be performed on a local processing device (e.g., a laptop).

The physician servers 121, hospital servers 122, clinical trial servers 123, research lab servers 124, and/or laboratory information systems 125 refer to systems used by pathologists for reviewing the images of the slides. In hospital settings, tissue type information may be stored in one of the laboratory information systems 125.

Figure 1B:
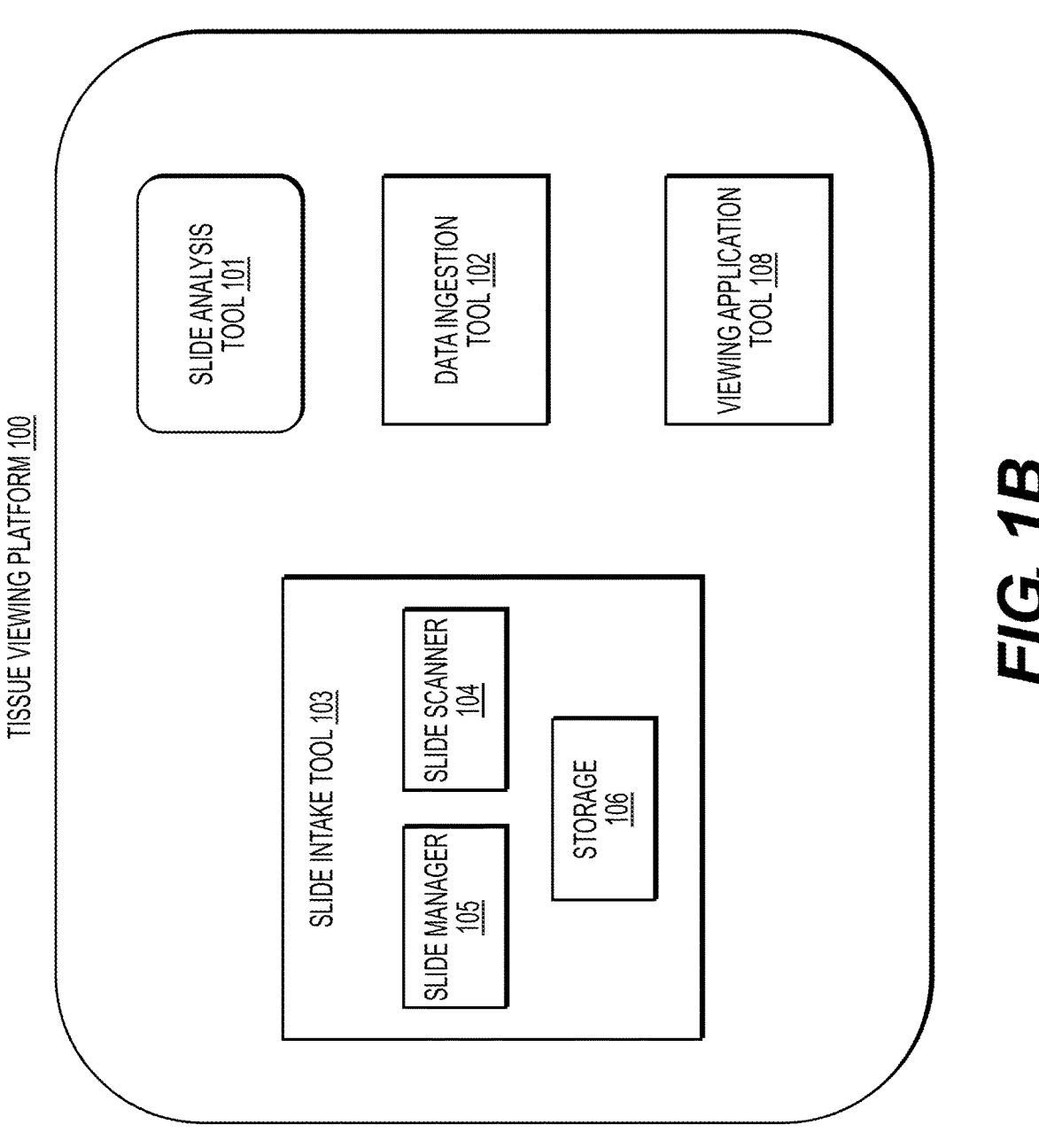
FIG. 1B illustrates an exemplary block diagram of a tissue viewing platform according to techniques presented herein.

FIG. 1B illustrates an exemplary block diagram of a tissue viewing platform 100 for determining specimen property of image property information pertaining to digital pathology image(s), using machine learning. For example, the tissue viewing platform 100 may include a slide analysis tool 101, a data ingestion tool 102, a slide intake tool 103, a slide scanner 104, a slide manager 105, a storage 106, and a viewing application tool 108.

The slide analysis tool 101, as described below, refers to a process and system for processing digital images associated with a tissue specimen, and using machine learning to analyze a slide, according to an exemplary embodiment.

The data ingestion tool 102 refers to a process and system for facilitating a transfer of the digital pathology images to the various tools, modules, components, and devices that are used for classifying and processing the digital pathology images, according to an exemplary embodiment.

The slide intake tool 103 refers to a process and system for scanning pathology images and converting them into a digital form, according to an exemplary embodiment. The slides may be scanned with slide scanner 104, and the slide manager 105 may process the images on the slides into digitized pathology images and store the digitized images in storage 106.

The viewing application tool 108 refers to a process and system for providing a user (e.g., a pathologist) with specimen property or image property information pertaining to digital pathology image(s), according to an exemplary embodiment. The information may be provided through various output interfaces (e.g., a screen, a monitor, a storage device, and/or a web browser, etc.).

The slide analysis tool 101, and each of its components, may transmit and/or receive digitized slide images and/or patient information to server systems 110, physician servers 121, hospital servers 122, clinical trial servers 123, research lab servers 124, and/or laboratory information systems 125 over an electronic network 120. Further, server systems 110 may include one or more storage devices 109 for storing images and data received from at least one of the slide analysis tool 101, the data ingestion tool 102, the slide intake tool 103, the slide scanner 104, the slide manager 105, and viewing application tool 108. Server systems 110 may also include processing devices for processing images and data stored in the storage devices. Server systems 110 may further include one or more machine learning tool(s) or capabilities, e.g., due to the processing devices. Alternatively or in addition, the present disclosure (or portions of the system and methods of the present disclosure) may be performed on a local processing device (e.g., a laptop).

Any of the above devices, tools and modules may be located on a device that may be connected to an electronic network 120, such as the Internet or a cloud service provider, through one or more computers, servers, and/or handheld mobile devices.

Figure 1C:
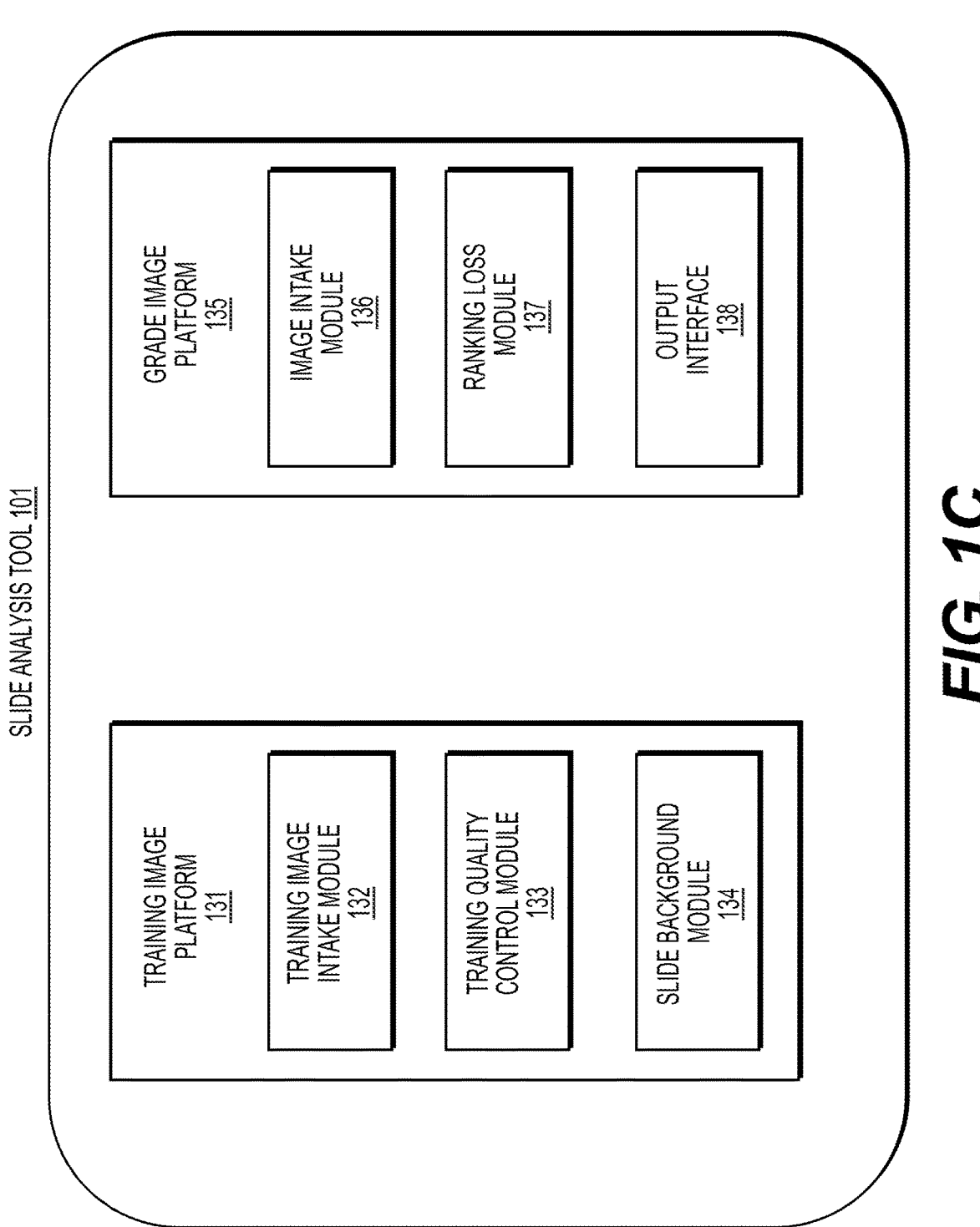
FIG. 1C illustrates an exemplary block diagram of a slide analysis tool, according to techniques presented herein.

FIG. 1C illustrates an exemplary block diagram of a slide analysis tool 201, according to an exemplary embodiment of the present disclosure. The slide analysis tool may include a training image platform 131 and/or a grade image platform 135.

The training image platform 131, according to one embodiment, may create or receive training images that are used to train a machine learning system to effectively analyze and classify digital pathology images. For example, the training images may be received from any one or any combination of the server systems 110, physician servers 121, hospital servers 122, clinical trial servers 123, research lab servers 124, and/or laboratory information systems 125. Images used for training may come from real sources (e.g., humans, animals, etc.) or may come from synthetic sources (e.g., graphics rendering engines, 3D models, etc.). Examples of digital pathology images may include (a) digitized slides stained with a variety of stains, such as (but not limited to) H&E, Hematoxylin alone, IHC, molecular pathology, etc.; and/or (b) digitized image samples from a 3D imaging device, such as micro-CT.

The training image intake module 132 may create or receive a dataset comprising one or more training images corresponding to either or both of images of a human and/or animal tissue and images that are graphically rendered. For example, the training images may be received from any one or any combination of the server systems 110, physician servers 121, and/or laboratory information systems 125. This dataset may be kept on a digital storage device. The training slide module 133 may intake training data that includes images and corresponding information. For example, training slide module 133 training data may include receiving one or more images (e.g., WSIs) of a human or animal. Training slide module 133 may also receive training data related to the Gleason score for each tissue corresponding to the digital images used for training. The training slide module 133 may include the ability to break an inputted WSI into tiles to perform further analysis of individual tiles of a WSI. The training slide module 133 may utilize convolutional neural network ("CNN"), Coord-Conv, Capsule network, Random Forest Support Vector Machine, Transformer trained directly with the appropriate loss function in order to help provide training for the machine learning techniques described herein. The slide background module 134 may analyze images of tissues and determine a background within a digital pathology image. It is useful to identify a background within a digital pathology slide to ensure tissue segments are not overlooked.

According to one embodiment, the grade image platform 135 may include an intake module 136, a ranking loss module 137, and an output interface 138. The inference platform 135 may receive a plurality of electronic images/additional information and apply one or more machine learning model to the received plurality of electronic images to output a Gleason score, Gleason scores for individual tiles of the images, and/or Gleason pattern score percentages for tiles and images. For example, the plurality of electronic images or additional information may be received from any one or any combination of the server systems 110, physician servers 121, hospital servers 122, clinical trial servers 123, research lab servers 124, and/or laboratory information systems 125. The intake module 136 may receive digital images (e.g., whole slide images) corresponding to one or more patients/individuals. Further, the digital images may correspond to an animal. Further, the intake module may receive metadata including a Gleason score information corresponding to the digital medical images. In other embodiments, the system may not receive Gleason score metadata when in use. The inference module 137 may apply one or more machine learning models to one or more digital images in order to identify an overall Gleason score as well as Gleason score percentages for images and tiles within images.

The output interface 138 may be used to output inputted images (e.g., to a screen, monitor, storage device, web browser, etc.) with Gleason score information. The output may include overall Gleason scores as well as percentages of each Gleason score present on an inputted image. Further, this may be performed and outputted at a tile level for images.

Grading cancer may be performed by comparing proportions of different sub-categories of cancer. For example, to determine a Gleason score, proportions of each Gleason pattern in prostate WSIs may be analyzed. Next, a two part score may be given to a WSI corresponding to the most dominant pattern and the most severe pattern present. The Gleason score then provides a measure for grading prostate cancer based on the presence of the sub-categories of cancer present on a WSI. For instance, a particular WSI may have 80% of a tissue be non-cancerous, 15% be considered Gleason score level 3 cancerous, and 5% Gleason score level 4 cancerous. This WSI would then have a Gleason score of 3+4.

Any cancer grading that involves computing proportions of different cancer sub-categories/grades can be formulated in terms of "greater than" and "less than" relations. All "greater than" relations can be converted to "less than" relations. For example, a "less than" relations for a 3+4 prostate cancer of a digital medical image is "proportions of Gleason pattern 4 is less than Gleason pattern 3". By defining the relationship of Gleason patterns as "less than" relations, more information may be obtained from a sample. For example, "3+4" means there is more grade 3 than grade 4, or alternatively there is less grade 4 than grade 3. Both could be incorporated into the training signals to the network to provide more information while training the machine learning algorithm.

The digital medical image may be broken down into a set of tiles, each representing a section of an image. For example, an image may be broken into a 10×10 set of tiles. Each tile may be assigned one or more Gleason scores or indicate non-cancer. When examining a digital medical image with a Gleason score, the score does not indicate tile-level pattern annotations, only an overall score. The system described herein can imply greater than and less than relation between Gleason patterns when given a Gleason score. For example, a 3+4 Gleason score may imply: there are two or more tiles with Gleason pattern 3 in the image; there is at least one tile with Gleason pattern 4 in the image, the total number of tiles with Gleason pattern 3 is more than the total number of tiles with Gleason pattern 4; there are no tiles with Gleason pattern 5 (i.e., the number of tiles with Gleason pattern 5 is less than one); and there may be some benign tiles in the slide (i.e., the number of tiles that are benign is greater than variable T). The information (e.g., the greater than and less than equations) may be translated to ranking losses. Given nine Gleason scores and one benign class, there may be ten sets of ranking losses.

Regarding the Gleason scores being converted to logical rules, "count(GPx)" may roughly denote the number of GPx tiles in the slide (GP referring to Gleason pattern). Thus count (GP3) may refer to how many tiles are marked as Gleason pattern 3, count(GP4) refers to how many tiles are marked as Gleason pattern 4, and count (GP5) refers to how many tiles are marked as Gleason pattern 5. Counting may be done implicitly by computing the sum of softmax output of each tile. The softmax output may refer to the probability distribution of the network and may be a vector that sums to one. The actual implementation may be different. $S_{max}$ may refer to the maximum count score of a GP (e.g., 0.5). $S_{min}$ may refer to the minimum counts score of a GP (e.g., 0.08). N may refer to the total number of tiles in a slide. $S_{benign}$ may refer to the minimum score of benign (e.g., 0.01N).

Below are the greater than and less than equations that may be created for each potential Gleason score assigned to a digital medical image. The potential scores (and benign) that may be used to grade prostate cancer are: benign, 3+3, 3+4, 3+5, 4+4, 4+3, 4+5, 5+5, 5+4, and 5+3. The greater than and less than equations for each score are exampled as follows:

The equations corresponding to a Gleason score of "benign" are:

$$Count(benign)<0.9N$$

$$Count(GP3)<S_{max}$$

$$Count(GP4)<S_{max}$$

$$Count(GP5)<S_{max}$$

The equations corresponding to a Gleason score of "3+3" are:

$$Count(GP3)>S_{min}$$

$$Count(GP4)<S_{max}$$

$$Count(GP5)<S_{max}$$

$$Count(GP3)>>Count(GP4)(auxiliary)$$

$$Count(GP3)>>Count(GP5)(auxiliary)$$

$$Count(benign)>S_{benign}$$

The equations corresponding to a Gleason score of "3+4" are:

$$Count(GP5)<S_{max}$$

$$Count(GP3)>Count(GP4)$$

$$Count(GP4)>S_{min}$$

$$Count(GP3)>S_{min}$$

$$Count(GP4)>>Count(GP5)(auxiliary)$$

$$Count(benign)>S_{benign}$$

The equations corresponding to a Gleason score of "3+5" are:

$$Count(GP3)>S_{min}$$

$$Count(GP3)>Count(GP5)$$

$$Count(GP5)>S_{min}$$

$$Count(GP3)>Count(GP4)$$

$$Count(benign)>S_{benign}$$

The equations corresponding to a Gleason score of "4+4" are:

$$Count(GP4)>S_{min}$$

$$Count(GP3)<S_{max}$$

$$\text{Count}(GP5) < S_{max}$$

$$\text{Count}(GP4) >> \text{Count}(GP3)(\text{auxiliary})$$

$$\text{Count}(GP4) >> (GP5)(\text{auxiliary})$$

$$\text{Count}(\text{benign}) > S_{benign}$$

The equations corresponding to a Gleason score of "4+3" are:

$$\text{Count}(GP5) < S_{max}$$

$$\text{Count}(GP4) > \text{Count}(GP3)$$

$$\text{Count}(GP3) > S_{min}$$

$$\text{Count}(GP4) > S_{min}$$

$$\text{Count}(GP4) > \text{Count}(GP5)(\text{auxiliary})$$

$$\text{Count}(\text{benign}) > S_{benign}$$

The equations corresponding to a Gleason score of "4+5" are:

$$\text{Count}(GP4) > S_{min}$$

$$\text{Count}(GP4) > \text{Count}(GP5)$$

$$\text{Count}(GP5) > S_{min}$$

$$\text{Count}(GP4) > \text{Count}(GP3)$$

$$\text{Count}(\text{benign}) > S_{benign}$$

The equations corresponding to a Gleason score of "5+5" are:

$$\text{Count}(GP5) > S_{min}$$

$$\text{Count}(GP3) < S_{max}$$

$$\text{Count}(GP4) < S_{max}$$

$$\text{Count}(GP5) > \text{Count}(GP3)(\text{auxiliary})$$

$$\text{Count}(GP5) > \text{Count}(GP4)(\text{auxiliary})$$

$$\text{Count}(\text{benign}) > S_{benign}$$

The equations corresponding to a Gleason score of "5+4" are:

$$\text{Count}(GP5) > \text{Count}(GP4)$$

$$\text{Count}(GP5) > S_{min}$$

$$\text{Count } GP4) > S_{min}$$

$$\text{Count}(GP5) > \text{Count}(GP3)$$

$$\text{Count}(\text{benign}) > S_{benign}$$

The equations corresponding to a Gleason score of "5+3" are:

$$\text{Count}(GP5) > \text{Count}(GP3)$$

$$\text{Count}(GP5) > S_{min}$$

$$\text{Count}(GP3) > S_{max}$$

$$\text{Count}(GP4) < S_{max}$$

$$\text{Count}(\text{benign}) > S_{benign}$$

Next, each logical rule can be translated to a less than equation exampled below. These may be referred to as minimization problems.

The logical rules to minimization problems corresponding to a Gleason score of "benign" are:

$$0.9N - \text{Count}(\text{benign}) < 0$$

$$\text{Count}(GP3) - S_{max} < 0$$

$$\text{Count}(GP4) - S_{max} < 0$$

$$\text{Count}(GP5) - S_{max} < 0$$

The logical rules to minimization problems corresponding to a Gleason score of "3+3" are:

$$S_{min} - \text{Count}(GP3) < 0$$

$$\text{Count}(GP4) - S_{max} < 0$$

$$\text{Count}(GP5) - S_{max} < 0$$

$$\text{Count}(GP4) - \text{Count}(GP3) << 0(\text{auxiliary})$$

$$\text{Count}(GP5) - \text{Count}(GP3) << 0(\text{auxiliary})$$

$$S_{benign} - \text{Count}(\text{benign}) < 0$$

The logical rules to minimization problems corresponding to a Gleason score of "3+4" are:

$$\text{Count}(GP5) - S_{max} < 0$$

$$\text{Count}(GP4) - \text{Count}(GP3) < 0$$

$$S_{min} - \text{Count}(GP4) < 0$$

$$S_{min} - \text{Count}(GP3) < 0$$

$$\text{Count}(GP5) - \text{Count}(GP4) << 0(\text{auxiliary})$$

$$S_{benign} - \text{Count}(\text{benign}) < 0$$

The logical rules to minimization problems corresponding to a Gleason score of "3+5" are:

$$S_{min} - \text{Count}(GP3) < 0$$

$$\text{Count}(GP5) - \text{Count}(GP3) < 0$$

$$S_{min} - \text{Count}(GP5) < 0$$

$$\text{Count}(GP4) - \text{Count}(GP3) < 0$$

$$S_{benign} - \text{Count}(\text{benign}) < 0$$

The logical rules to minimization problems corresponding to a Gleason score of "4+4" are:

$$S_{min} - \text{Count}(GP4) < 0$$

$$\text{Count}(GP3) - S_{max} < 0$$

$$\text{Count}(GP5) - S_{max} < 0$$

$$\text{Count}(GP3) - \text{Count}(GP4) << 0(\text{auxiliary})$$

$$\text{Count}(GP5) - \text{Count}(GP4) << 0(\text{auxiliary})$$

$$S_{benign} - \text{Count}(\text{benign}) < 0$$

The logical rules to minimization problems corresponding to a Gleason score of "4+3" are:

$$\text{Count}(GP5) - S_{max} < 0$$

$$\text{Count}(GP3) - \text{Count}(GP4) < 0$$

$S_{min}$–Count($GP3$)<0

$S_{min}$–Count($GP4$)>0

Count($GP5$)–Count($GP4$)<0(auxiliary)

$S_{benign}$–Count(benign)<0

The logical rules to minimization problems corresponding to a Gleason score of "4+5" are:

$S_{min}$–Count($GP4$)<0

Count($GP5$)–Count($GP4$)<0

$S_{min}$–Count($GP5$)<0

Count($GP3$)–Count($GP4$)<0

$S_{benign}$–Count(benign)<0

The logical rules to minimization problems corresponding to a Gleason score of "5+5" are:

$S_{min}$–Count($GP5$)<0

Count($GP3$)–$S_{max}$<0

Count($GP4$)–$S_{max}$<0

Count($GP3$)–Count($GP5$)<0(auxiliary)

Count($GP4$)–Count($GP5$)<0(auxiliary)

$S_{benign}$–Count(benign)<0

The logical rules to minimization problems corresponding to a Gleason score of "5+4" are:

Count($GP4$)–Count($GP5$)<0

$S_{min}$–Count($GP5$)<0

$S_{min}$–Count $GP4$)<0

Count($GP3$)–Count($GP5$)<0

$S_{benign}$–Count(benign)<0

The logical rules to minimization problems corresponding to a Gleason score of "5+3" are:

Count($GP3$)–Count($GP5$)<0

$S_{min}$–Count($GP5$)<0

$S_{max}$–Count($GP3$)<0

Count($GP4$)–$S_{max}$<0

$S_{benign}$–Count(benign)<0

Next a loss function was created to address the minimization problem. The minimization problems may be of the following form:

Err<0 s.t err=$a$–$b$

In terms of a loss function, if e (e.g., the error) is smaller than zero the loss should be close to zero and a large number otherwise.

Figure 2:
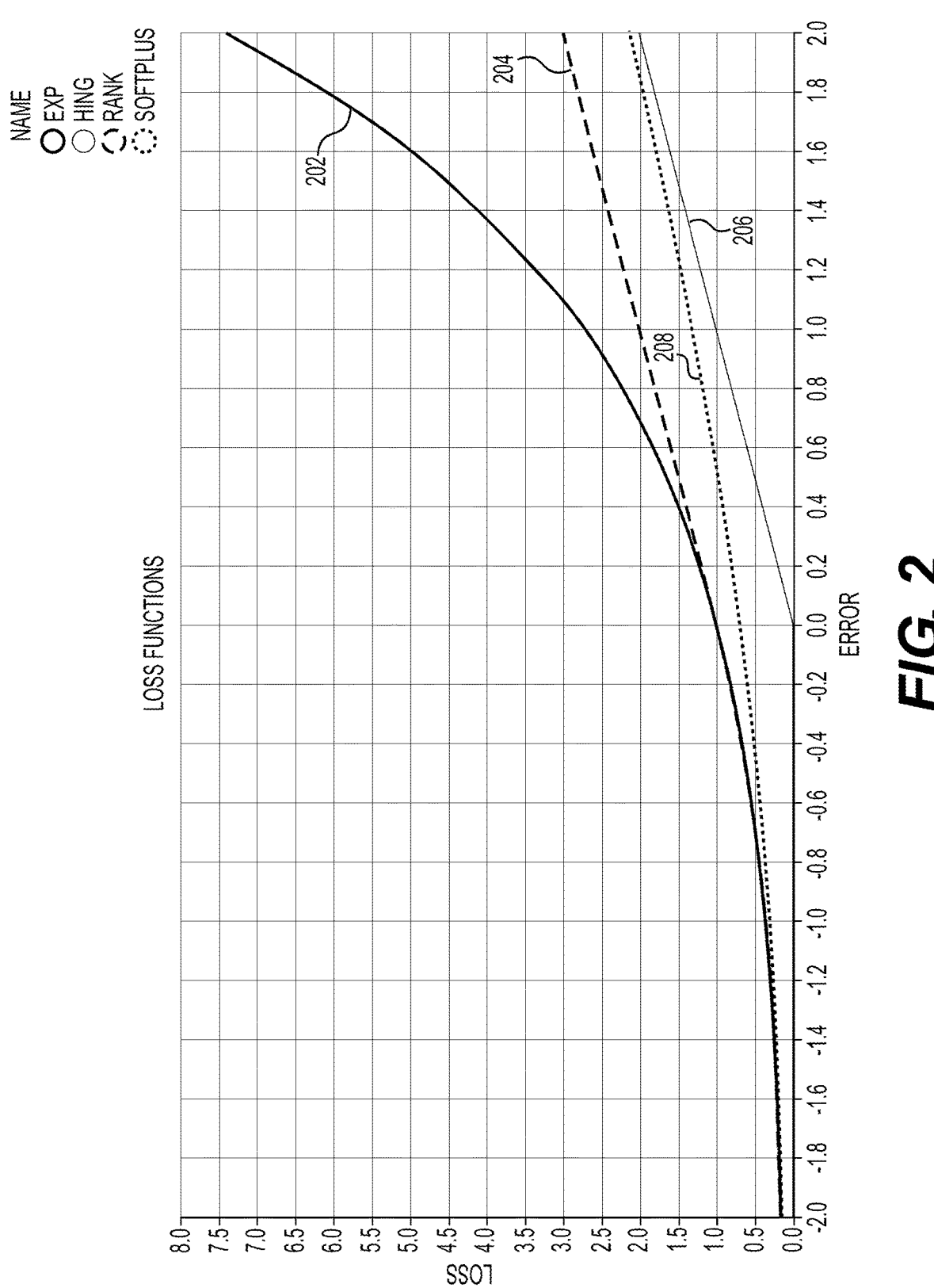
FIG. 2 illustrates an exemplary set of functions to formulate "less than" relations.

Next, each "less than" relation can be formulated to a loss function using one of following functions provided in FIG. 2. By formulating the loss function, the relationships provided above may be converted into a signal for training the neural network described herein. The loss may measure how well the network is predicting the ranking. The loss function may minimize the loss during training of the machine learning system.

FIG. 2 illustrates an exemplary set of functions to formulate "less than" relations. The X axis plots error and the Y axis plots loss. The function lines are exponential loss 202, ranking 204, softplus loss 206, and hinge loss 208. The exponential loss function 202 may be defined as: $L_{exp}$(err)= $e^{err}$. The hinge loss function 208 may be defined as $L_{hing}$ (err)=max (0, a+err). The softplus loss function 206 may be defined as $L_{softplus}$(err)=log (1+$L_{exp}$(+err). As will be described in greater detail below, the ranking formula 204 may be utilized to train the system described herein.

Examining the hinge loss 208 the hinge loss becomes zero if err>>0, that in turns makes its derivative zero in the negative region. As a result, as soon as the error becomes smaller than negative, the error signal becomes zero and the network does not learn from the data. In contrast, both the exponential loss function 202 and the softplus loss function 206 become zeros in the infinity direction. This means that even though the loss approaches zero in the negative region, it will always generate error signals. One major difference between the exponential loss function 202 and softplus loss function 206 is that error signals in the positive region are stronger using the softplus loss function 206. A potential issue with the exponential loss function 202 is that it may generate undefined or unrepresentable values of x. For example, the inequality 0.9N–count (benign)<0 where N=300 to: ($L_{exp}$ (0.9N–count (benign))=$L_{exp}$ (0.9*300–0)= $e^{2700}$. $e^{2700}$ will be considered undefined or unrepresented, because although the value is numerically possible to compute, its gradient would be too high of a value.

Based on the problems above, the ranking function 204 was created. The ranking function 204 may be defined as $L_{rank}$=x+1 if x>0 & $L_{rank}$=$e^x$ if x≤0. The ranking function 204 is differentiable everywhere, becomes zero in the –inf, the gradient becomes zero in the –inf, and has a maximum gradient equal to 1.

In an alternative embodiment, the exponential loss function 202 may be utilized to train the machine learning system described herein. In this embodiment, the aggregated scores may be normalized or compressed. The aggregated scores may be normalized based on the tissue tile counts of each slide or sum of being GP3, GP4, and GP5 scores.

The total loss of the Gleason scores may be calculated given a Gleason score with k minimization rules (i.e., inequities). Given a set of "less than" relations for each grade of cancer, the total loss of the model may be equal to the sum of all "less than" relations. The total loss of a Gleason score may be calculated as: $L_{total}$=$\Sigma_{i=k}^{k}L_{rank}$(rule$_i$). The $L_{rank}$(rule$_i$) may define the ability to model each less than relationship and $L_{total}$ defines the total loss across all less than relationships.

Further, the system may utilize a shifted ranking loss in an alternative embodiment. Assuming the inequity "count (gp3)–$S_{max}$<0" where the network is instructed to count zero number of GP3 tiles in the given slide. With this assumption, the minimum value of count(GPx) is zero and $S_{max}$ should be a value less than 1 to make sure the network does not predict a tile with a high GP3 score in the above case. Assuming we set $S_{max}$=0.5 and taking into account that count(GP3) is zero, "count(gp3)–$S_{max}$=–0.5". According to the plot of $L_{rank}$, the loss value and gradient will be high in this specific scenario even though the network holds the inequity. To address this problem, the following shift parameter may be introduced: $L_{rank}=x+b+1$ if $x+b>0$ & $L_{rank}=e^{x+b}$ if $x+b<0$. By default, $b=0$ is the original $L_{rank}$. B may be set to a negative value in inequities similar to above to make sure the loss value and its gradient are close to zero.

A PNI positive WSI means there is at least one tissue tile in the WSI that resembles PNI. This statement can be formulated using "greater than" relation and converted to a "less than" relation. Then, the "less than" relation may be formulated using the ranking loss function and utilized for training the model.

FIG. 3A is a flowchart illustrating an example method for training an algorithm that uses a loss function to train a grading machine learning model, according to techniques presented herein.

In another embodiment, the system may be utilized to predict whether cancer is located on a WSI. A cancer positive WSI means there may be at least one tissue tile that has cancer. In another embodiment, as discussed in greater detail in FIG. 4A and FIG. 4B, the system may be utilized to predict Gleason scores. In another embodiment, the system may be utilized to determine whether perineal invasion (PNI) is present. Similar the cancer embodiment, a PNI positive WSI means there may be at least one tissue tile that has PNI present.

First, at step 302, the system may determine a set of less than relations. For example, this may be the less than relations meant to define the Gleason scores above. In another example, the less than relationship may be whether cancer is present or not. In another example, the less than relationship may be whether PNI is present or not.

Next at step 304, the system may formulate each less than relation using a loss function. In one example, the loss function may be ranking loss function 204.

Next at step 306, the system may receive one or more digital medical images (e.g., WSI of an autopsy pathology specimen, magnetic resonance imaging (MRI), computed tomography (CT), positron emission tomography (PET), mammogram, etc.). Further, the system may receive metadata corresponding to the digital medical image. For example, metadata may include, but is not limited to whether cancer is present, a Gleason score, and/or ground-truth labels and proportions of cancer. The metadata may further indicate whether PNI is present.

Next at step 308, the system may divide the received images from step 306 into tiles. Next, the system may, using a machine learning system, predict proportions of each cancer sub-category (e.g., Gleason pattern or whether cancer is present). In another example, the machine learning system may predict whether PNI is present.

Next at step 310, the system may compute the loss for each "less than" relation using the ground-truth label and proportion metadata received at step 306.

Last, at step 312, the system may compute the total loss, compute the backward pass, and update the grading machine learning model. The training may include penalizing the machine learning system when the formulated loss function creates error values greater than zero. The loss function may be trained to create error values as small (and negative) as possible. The trained grading machine learning model may be capable of outputting a digital medical image with proportions of cancer, locations of cancer (e.g., a segmentation mask with grades of cancer) and a cancer score (e.g., cancer is present and/or a Gleason score). Thus, the system uses weak-labels (e.g., weak supervision) to learn more granular labels using the re-formulation and ranking loss formula.

In another example, the system may be capable of outputting a digital medical image with proportions and the location of PNI on the digital medical images.

Figure 3B:
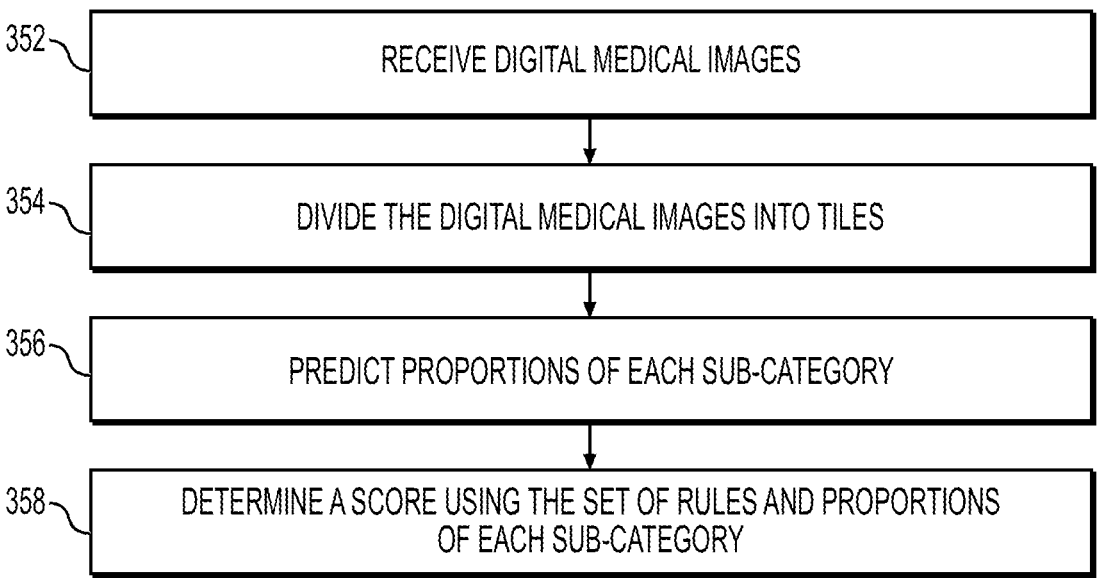
FIG. 3B is a flowchart illustrating an example method for using an algorithm that uses a grading model to identify sub-classes within a digital image, according to techniques presented herein.

FIG. 3B is a flowchart illustrating an example method for using an algorithm that uses a grading model to identify sub-classes within a digital image, according to techniques presented herein.

At step 352, the system may first receive digital medical images.

Next, at step 354, the system may divide the digital medical images into tiles.

Next, at step 356, the system may utilize the trained machine learning model from step 312 to predict the proportions of each sub-category (e.g., Gleason patterns, areas with cancer, and/or areas with PNI). This may include the trained machine learning system analyzing each tile of a particular digital medical images to determine whether cancer is present and/or a grading score. The trained machine learning system may then determine how many tiles are benign or cancerous, and if cancerous, the system may determine what grade of cancer is dominant on each tile. In another example, this may include the trained machine learning system analyzing each tile of a particular digital medical images to determine whether PNI.

Last, at step 358, the system may deduce the grade of cancer using the set of rules and proportion of each cancer sub-category. For example, the system may track and count the total tiles that are benign as well as total tiles that have cancer present. Further, the system may record and save the grades of cancer present for each tile. Lastly, the system may then be capable of outputting a cancer score (e.g., whether cancer is present, or outputting a Gleason score), a segmentation mask with the location and cancer and/or cancer grades, and proportions of cancer compared to non-cancer, as well as proportions of each grade of cancer.

In another example, at step 358, the system may determine what proportion of tiles contain PNI. For example, the system may track and count the total tiles that are benign as well as total tiles that have PNI present. The system may then be capable of outputting whether PNI is present, a PNI segmentation mask with the location of PNI, and the proportion of the digital medical image that includes PNI.

Currently, a Gleason score is the gold standard to grade prostate cancer. A Gleason score is the sum of two numbers where the first number denotes the most dominant Gleason pattern ("Gp") and the second indicates the most severe Gp in a WSI.

Based on this, a 3+4 Gleason score may mean: There are two or more GP3 tiles in the slide (i.e., the number of GP3 tiles is greater than 2); there is at least one GP4 tile in the slide (i.e., the number of GP4 tiles is greater than 1); the total number of GP3 tiles is greater than the total number of GP4 tiles; there is no GP5 tile in the slide (i.e., the number of GP5 tiles is less than 1); and there might be some benign tiles in the slide (i.e., the number of benign tiles is greater than T).

Each Gleason score has its own set of rules that define the Gleason patterns. Once these rules are defined for each Gleason score, they may be converted to "less than" relations and each of relation is formulated using the ranking loss. These losses that the system outputs may then be used to train the model to perform Gleason score prediction. This may allow for the model to be trained based on proportions of Gleason patterns rather than on scores.

FIG. 4A is a flowchart illustrating an example method for training an algorithm that uses a loss function to train a grading model based on various sub-classes of cancer, according to techniques presented herein.

First, at step 402, the system may determine a set of less than relations. The less than relations may be the ten sets of less than relations meant to define the Gleason scores described above.

Next at step 404, the system may formulate each less than relation using a loss function. In one example, the loss function may be ranking loss function 204.

Next at step 406, the system may receive one or more digital medical images (e.g., WSI of an autopsy pathology specimen, magnetic resonance imaging (MRI), computed tomography (CT), positron emission tomography (PET), mammogram, etc.). Further, the system may receive meta-data corresponding to the digital medical image. For example, metadata may include, but is not limited to whether cancer is present, a Gleason score, and/or ground-truth labels and proportions of cancer.

Next at step 408, the system may divide the received images from step 406 into tiles. Next, the system may, using a machine learning system, predict proportions of each Gleason pattern sub-category for each tile.

Next at step 410, the system may compute the loss for each "less than" relation using the ground-truth label and proportion metadata received at step 406.

Figure 4B:
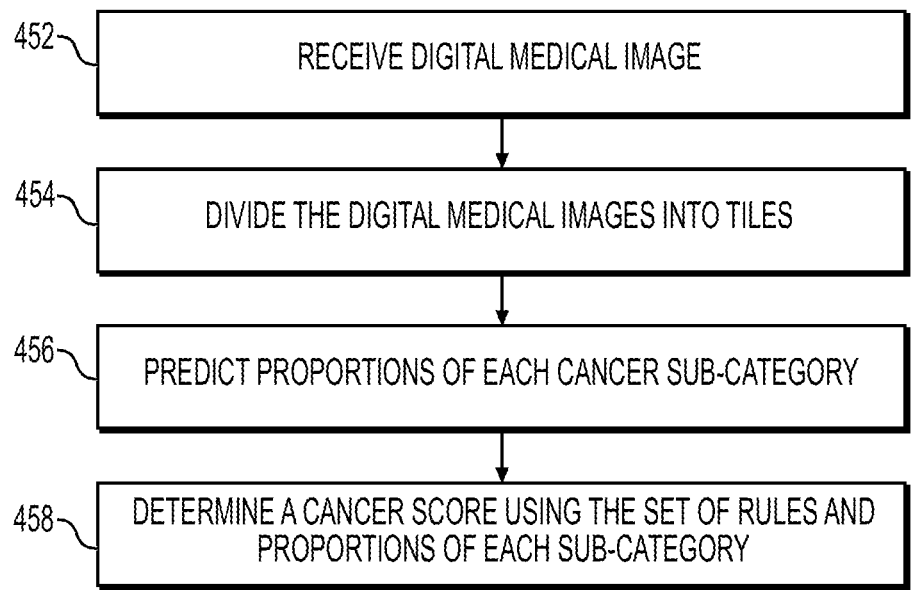
FIG. 4B is a flowchart illustrating an example method for using an algorithm that uses a grading model to identify cancer sub-classes within a digital image, according to techniques presented herein.

Last, at step 412, the system may compute the total loss, compute the backward pass, and update the grading machine learning model. The trained grading machine learning model may be capable of outputting a digital medical image with proportions of cancer, locations of cancer (e.g., a segmentation mask with grades of cancer) and a Gleason score. Thus, the system uses weak-labels (e.g., weak supervision) to learn more granular labels using the re-formulation and ranking loss formula FIG. 4B is a flowchart illustrating an example method for using an algorithm that uses a grading model to identify cancer sub-classes within a digital image, according to techniques presented herein.

At step 452, the system may first receive digital medical images.

Next, at step 454, the system may divide the digital medical images into tiles.

Next, at step 456, the system may utilize the trained machine learning model from step 412 to predict the proportions of each Gleason pattern. This may include the trained machine learning system analyzing each tile of a particular digital medical images to determine a Gleason score level for each tile. The trained machine learning system may then determine how many tiles are benign or cancerous, and if cancerous, the system may determine what grade of cancer is dominant on each tile.

Last, at step 458, the system may deduce the Gleason score using the set of rules and proportion of each cancer sub-category. For example, the system may track and count the total tiles that are benign as well as the amount of tile contain each Gleason grade. Lastly, the system may then be capable of outputting a cancer grade (e.g., whether cancer is present, or outputting a Gleason score), a segmentation mask with the location and cancer grades, and proportions of cancer compared to non-cancer, as well as proportions of each grade of cancer.

FIG. 5 is a flowchart illustrating an example method for determining cancer subclasses using a machine learning system trained by ranking loss, according to techniques presented herein.

At step 502, the system may receive one or more medical images of at least one pathology specimen, the pathology specimen being associated with a patient.

At step 504, the system may divide the one or more medical images into a plurality of tiles.

At step 506, the system may predict, using a machine learning system, proportions of each type of cancer sub-category for the plurality of tiles, the machine learning system having been trained by ranking loss At step 508, the system may determine an overall grade of cancer for the one or more medical images.

Figure 6:
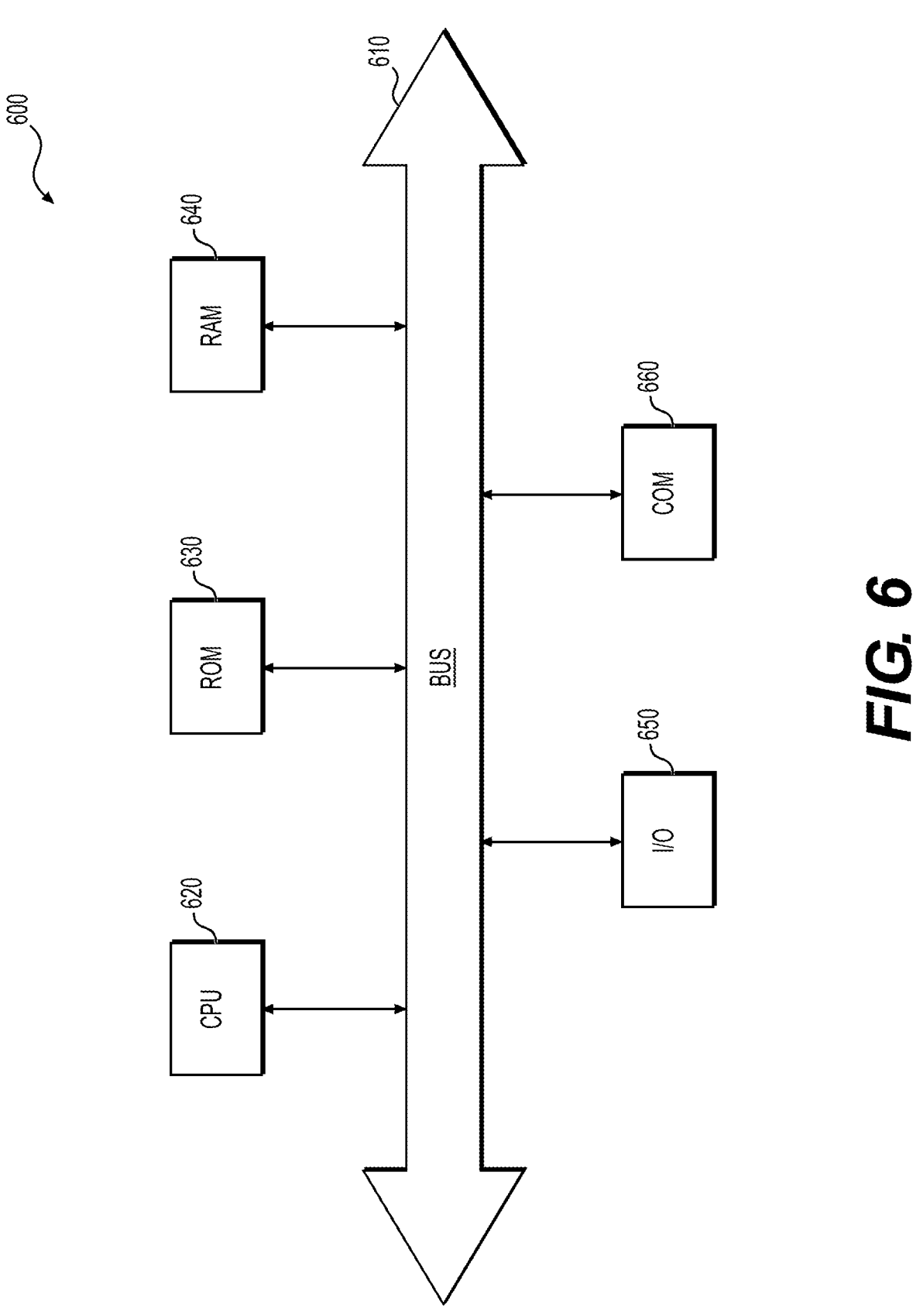
FIG. 6 depicts an example of a computing device that may execute techniques presented herein, according to one or more embodiments.

As shown in FIG. 6, device 600 may include a central processing unit (CPU) 620. CPU 620 may be any type of processor device including, for example, any type of special purpose or a general-purpose microprocessor device. As will be appreciated by persons skilled in the relevant art, CPU 620 also may be a single processor in a multi-core/multi-processor system, such system operating alone, or in a cluster of computing devices operating in a cluster or server farm. CPU 620 may be connected to a data communication infrastructure 610, for example a bus, message queue, network, or multi-core message-passing scheme.

Device 600 may also include a main memory 640, for example, random access memory (RAM), and also may include a secondary memory 630. Secondary memory 630, for example a read-only memory (ROM), may be, for example, a hard disk drive or a removable storage drive. Such a removable storage drive may comprise, for example, a floppy disk drive, a magnetic tape drive, an optical disk drive, a flash memory, or the like. The removable storage drive in this example reads from and/or writes to a removable storage unit in a well-known manner. The removable storage may comprise a floppy disk, magnetic tape, optical disk, etc., which is read by and written to by the removable storage drive. As will be appreciated by persons skilled in the relevant art, such a removable storage unit generally includes a computer usable storage medium having stored therein computer software and/or data.

In alternative implementations, secondary memory 630 may include similar means for allowing computer programs or other instructions to be loaded into device 600. Examples of such means may include a program cartridge and cartridge interface (such as that found in video game devices), a removable memory chip (such as an EPROM or PROM) and associated socket, and other removable storage units and interfaces, which allow software and data to be transferred from a removable storage unit to device 600.

Device 600 also may include a communications interface ("COM") 660. Communications interface 660 allows software and data to be transferred between device 600 and external devices. Communications interface 660 may include a modem, a network interface (such as an Ethernet card), a communications port, a PCMCIA slot and card, or the like. Software and data transferred via communications interface 660 may be in the form of signals, which may be electronic, electromagnetic, optical or other signals capable of being received by communications interface 660. These signals may be provided to communications interface 660 via a communications path of device 600, which may be implemented using, for example, wire or cable, fiber optics, a phone line, a cellular phone link, an RF link or other communications channels.

The hardware elements, operating systems, and programming languages of such equipment are conventional in nature, and it is presumed that those skilled in the art are adequately familiar therewith. Device 600 may also include input and output ports 650 to connect with input and output devices such as keyboards, mice, touchscreens, monitors, displays, etc. Of course, the various server functions may be implemented in a distributed fashion on a number of similar platforms, to distribute the processing load. Alternatively, the servers may be implemented by appropriate programming of one computer hardware platform.

Throughout this disclosure, references to components or modules generally refer to items that logically may be grouped together to perform a function or group of related functions. Like reference numerals are generally intended to refer to the same or similar components. Components and/or modules may be implemented in software, hardware, or a combination of software and/or hardware.

The tools, modules, and/or functions described above may be performed by one or more processors. "Storage" type media may include any or all of the tangible memory of the computers, processors or the like, or associated modules thereof, such as various semiconductor memories, tape drives, disk drives and the like, which may provide non-transitory storage at any time for software programming.

Software may be communicated through the Internet, a cloud service provider, or other telecommunication networks. For example, communications may enable loading software from one computer or processor into another. As used herein, unless restricted to non-transitory, tangible "storage" media, terms such as computer or machine "readable medium" refer to any medium that participates in providing instructions to a processor for execution.

The foregoing general description is exemplary and explanatory only, and not restrictive of the disclosure. Other embodiments may be apparent to those skilled in the art from consideration of the specification and practice of the invention disclosed herein. It is intended that the specification and examples be considered as exemplary only.

What is claimed is:

1. A computer-implemented method for processing electronic medical images, comprising:
   receiving one or more medical images of at least one pathology specimen associated with a patient;
   dividing the one or more medical images into a plurality of tiles;
   predicting, using a machine learning system, proportions of each type of cancer sub-category for the plurality of tiles, the machine learning system having been trained by ranking loss, the machine learning system having been trained by:
   dividing a plurality of electronic images into tiles; and
   for each of the plurality of electronic images:
      predicting proportions of any of a plurality of cancer sub-categories;
      determining a loss for each less than relation based on ground-truth proportions;
      determining a total loss based on the loss for each less than relation;
      determining a backward pass; and
      updating the machine learning system using the total loss and backward pass; and
   determining an overall grade of cancer for the one or more medical images.

2. The method of claim 1, wherein the overall grade of cancer is output as a Gleason score prediction.

3. The method of claim 1, wherein predicting proportions of each type of cancer includes predicting proportions of each cancer sub-category.

4. The method of claim 3, wherein during training, the ranking loss is determined for each cancer sub category.

5. The method of claim 4, wherein the total ranking loss of the machine learning system is calculated using a ranking loss formula Lrank=x+1 if x>0 & Lrank=ex if x<0.

6. The method of claim 5, wherein the machine learning system is trained using weak labels to learn more granular labels using the rank loss formula.

7. The method of claim 3, further comprising:
   outputting the proportion of each cancer sub-category.

8. The method of claim 1, further comprising:
   outputting a segmentation map displaying a location of each cancer sub-category.

9. A system for processing electronic medical images, the system comprising:
   at least one memory storing instructions; and
   at least one processor configured to execute the instructions to perform operations comprising:
      receiving one or more medical images of at least one pathology specimen associated with a patient;
      dividing the one or more medical images into a plurality of tiles;
      predicting, using a machine learning system, proportions of each type of cancer sub-category for the plurality of tiles, the machine learning system having been trained by ranking loss, the machine learning system having been trained by:
         dividing a plurality of electronic images into tiles; and
         for each of the plurality of electronic images:
            predicting proportions of any of a plurality of cancer sub-categories;
            determining a loss for each less than relation based on ground-truth proportions;
            determining a total loss based on the loss for each less than relation;
            determining a backward pass; and
            updating the machine learning system using the total loss and backward pass; and
      determining an overall grade of cancer for the one or more medical images.

10. The system of claim 9, wherein the overall grade of cancer is output as a Gleason score prediction.

11. The system of claim 9, wherein predicting proportions of each type of cancer includes predicting proportions of each cancer sub-category.

12. The system of claim 11, wherein during training, the ranking loss is determined for each cancer sub category.

13. The system of claim 12, wherein the total ranking loss of the machine learning system is calculated using a ranking loss formula Lrank=x+1 if x>0 & Lrank=ex if x<0.

14. The system of claim 13, wherein the machine learning system is trained using weak labels to learn more granular labels using the rank loss formula.

15. The system of claim 11, further comprising:
   outputting the proportion of each cancer sub-category.

16. The system of claim 9, further comprising:
   outputting a segmentation map displaying a location of each cancer sub-category.

17. A non-transitory computer-readable medium storing instructions that, when executed by a processor, perform operations processing electronic digital medical images, the operations comprising:
   receiving one or more medical images of at least one pathology specimen associated with a patient;
   dividing the one or more medical images into a plurality of tiles;
   predicting, using a machine learning system, proportions of each type of cancer sub-category for the plurality of tiles, the machine learning system having been trained by ranking loss, the machine learning system having been trained by:

dividing a plurality of electronic images into tiles; and
for each of the plurality of electronic images:
  predicting proportions of any of a plurality of cancer
    sub-categories;
  determining a loss for each less than relation based
    on ground-truth proportions;
  determining a total loss based on the loss for each
    less than relation;
  determining a backward pass; and
  updating the machine learning system using the total
    loss and backward pass; and
determining an overall grade of cancer for the one or more
    medical images.

18. The non-transitory computer-readable medium of claim 17, wherein the overall grade of cancer is output as a Gleason score prediction.

19. The non-transitory computer-readable medium of claim 17, wherein predicting proportions of each type of cancer includes predicting proportions of each cancer sub-category.

20. The non-transitory computer-readable medium of claim 17, wherein during training, the ranking loss is determined for each cancer sub category.

* * * * *